United States Patent [19]

Fumagalli et al.

[11] 4,061,868

[45] Dec. 6, 1977

[54] PROCESS FOR THE MANUFACTURE OF GLYCOLS AND GLYCOL NONO-ESTERS

[75] Inventors: Carlo Fumagalli, Sirone (Como); Giuseppe Caprara, Milan; Paolo Roffia, Mantova, all of Italy

[73] Assignee: Montedison S.p.A., Milan, Italy

[21] Appl. No.: 616,602

[22] Filed: Sept. 25, 1975

[30] Foreign Application Priority Data

Nov. 14, 1974 Italy .................................. 29433/74
July 11, 1975 Italy .................................. 25335/75

[51] Int. Cl.² ........................ C07C 67/05; C07C 29/04
[52] U.S. Cl. ................................ 560/246; 260/635 H; 560/112
[58] Field of Search ................ 260/497 R, 635 H

[56] References Cited

U.S. PATENT DOCUMENTS

| | | | |
|---|---|---|---|
| 1,982,545 | 11/1934 | Skarblom | 260/635 H |
| 2,071,395 | 2/1937 | Dreyfus | 260/635 H |
| 3,427,348 | 2/1969 | Olson | 260/635 H |
| 3,770,813 | 11/1973 | Kollar | 260/497 R |
| 3,928,474 | 12/1975 | Witheford | 260/635 H |

FOREIGN PATENT DOCUMENTS

| | | | |
|---|---|---|---|
| 44-8484 | 4/1969 | Japan | 260/635 H |
| 44-12127 | 6/1969 | Japan | 260/635 H |

*Primary Examiner*—James O. Thomas, Jr.
*Assistant Examiner*—Michael Shippen
*Attorney, Agent, or Firm*—Morgan, Finnegan, Pine, Foley & Lee

[57] ABSTRACT

There is provided an improvement in the process for the preparation of organic monoesters of vicinal glycols and the corresponding free glycols by reacting an olefin with oxygen, water and a carboxylic acid, in the liquid phase, at an initial pH of lower than 7, the improvement comprising contacting the reaction mixture with a catalyst system consisting essentially of (i) iodine or an iodine compound selected from the group consisting essentially of copper iodide, manganese iodide, cerium iodide, an alkali metal iodide, an alkali earth metal iodide and the iodohydride of the olefin, (ii) a copper compound selected from the group consisting essentially of copper oxide, copper hydroxide, copper carbonate, copper iodide, and a copper salt of the carboxylic acid, and (iii) an activating ion selected from the group consisting of manganese cation, cerium cation, an alkali metal cation, an alkaline earth metal cation, nitric anion or a mixture of any of the foregoing, wherein the molar ratio of the carboxylic acid to water is lower than 1, the molar ratio of copper to water is equal to or lower than 2 moles of copper per 100 moles of water, and the molar ratio of iodine to copper is lower than 1.

12 Claims, No Drawings

PROCESS FOR THE MANUFACTURE OF GLYCOLS AND GLYCOL NONO-ESTERS

BACKGROUND OF THE INVENTION

Processes for the manufacture of organic monoesters of vicinal glycols and of the corresponding free glycols, by reaction in liquid phase, at a starting pH lower than 7, of the corresponding olefins with oxygen, with water and with the esterifying acid are already known.

In a process of the above-mentioned type, the catalytic use of copper and bromine is known, but the results thereby obtained are anything but satisfactory. The reaction rates are low; the consumptions are rather excessive; large amounts of undesired by-products are obtained such as the glycolic diesters, which make burdensom and complicated the final hydrolysis which is necessary in order to convert the raw reaction mixture into the more useful product, the glycol.

Still another drawback of the above-mentioned prior art process is the problem of corrosion due to the presence of bromine.

An object of this invention is that of limiting and possibly eliminating the above-mentioned drawbacks of the prior art processes. Other objects of this invention will become apparent from the description that follows.

GENERAL DESCRIPTION OF THE INVENTION

In its broadest form, the present invention concerns a process for the manufacture of organic monoesters of vicinal glycols and of the corresponding free glycol, by reaction in liquid phase, at an initial pH lower than 7 but preferably lower than 5, of the corresponding olefins with oxygen with water and with the esterifying acid, in the presence of iodine, copper and of at least one activating ion, according to the following molar ratios:

— acid: $H_2O$ = lower than 1 and preferably lower than 0.25;
— Cu: $H_2O$ = equal to or lower than 2 moles of Cu for 100 moles of $H_2O$;
— $I_2$ : Cu = Lower than 1 and preferably comprised between 0.1 and 0.5.

The activating ions which have yielded so far the best results are the cations of the transition metals cerium and manganese (and their mixtures) as well as the nitric anion ($NO_3^-$), optionally in combination with the above indicated cations.

Another group of activating ions is consisting of the alkali metal cations and of the alkline-earth metal cations.

The advantages deriving from this invention are considerable. First of all we have noted higher reaction rates and lower percentages of diesters by-products are obtained. Secondly, we have observed a consistent drop of the corrosive phenomena. A further advantage (with respect to the processes that contemplate anhydrous reaction conditions — see Ital. Pat. No. 876.118), is represented by a lower need of acid and by lower volumes in use of the acid itself.

Also, in the process of this invention is considering the hydrolysis downstream of the oxidation, there will be smaller quantity of reactants to be re-cycled and a limitation of their consumptions. Still another advantage of the present process is represented by the absence of vinyl and carbonyl by-products, which are formed when the catalytic system contains other elements, such as for instance palladium.

There are different ways to realize the catalytic system used in accordance with the present process. For instance, copper may be added in the form of either metal, oxide, hydroxide, carbonate, iodide or as the salt of the acid used. Said acid may be a carboxylic acid, more particularly acetic acid, or another organic acid such as formic, propionic, butyrric and benzoic acids.

Also iodine may be added under different forms; thus elementary iodine may be used, as well as copper iodide or the iodide of an activating cation, the iodohydrine of the olefin and more generally the iodo-derivatives of the compounds present in the reaction mixture.

There are different forms in which the activating cations may be added to the reaction mixture; the cations may be for instance formed 'in situ' from the metals added in a subdivided form, or they may be added in the form of oxides, hydroxides, carbonates, nitrates or iodides. Still another form is the salt of the used acid.

The anion may be added in the form of copper, cerium, manganese nitrates or of combinations thereof; moreover it may be formed 'in situ' by the addition of nitrogen oxides.

The reaction is applicable to quite a variety of olefins, including aliphatic olefins and in particular ethylene, propylene and butylene. Best results have been attained with ethylene.

The concentration of the olefin in the liquid phase is not critical and depends on the composition of the liquid phase and on the partial pressure in the gaseous phase, the limits of which pressure being imposed by the explosivity ranges.

As an oxidizing gas, air can be used, as well as oxygen or any other oxygen containing gas. Best results are attained with pure oxygen in the presence of inert diluents. Excellent results are achieved by using propane and, better still, ethane, acting as diluents.

Good results are obtained with mixtures of ethylene, ethane and oxygen, in which the molar percentage of the oxygen is comprised between 5 and 15%, while that of ethylene is comprised between 15% and 30%, the percentage of ethane being the complement to 100.

The temperature has a marked influence on the course of the reaction. Although the reaction may occur within the range of from 50° to 200° C, the most satisfactory results are attained when operating within the range of 130° and 160° C; below 130° C the reaction rate is too low, while above 160° C undesirable by-products are formed.

The pressure has a favourable influence on the reaction. It is possible to let the reaction take place at atmospheric pressure, although it is advisable to raise the pressure level above 10 atmospheres, up to a maximum of 200 atmospheres.

The residence time is depending on the reactants and on the operational conditions and should be substantially comprised between just a few minutes and 3-5 hours.

The products of the process according to the invention are to be considered amongst the most useful derivatives of the oil industry. Well known are for instance the use of ethylene glycol in the field of polyester fibers and of the anti-freeze mixtures.

SPECIFIC DESCRIPTION OF INVENTION

The following examples are given for better illustrating purposes, without limiting in any way the scope of the invention.

EXAMPLE 1

Into an enamelled 2400 cc autoclave, thermally stablilized and fitted with a rotating stirrer, baffles and reflux condenser, there were introduced:

| | |
|---|---|
| $I_2$ | 0.040 moles |
| $Cu(OCOCH_3)_2 \cdot H_2O$ | 0.300 moles |
| $Ce(OCOCH_3)_3$ | 0.250 moles |
| $CH_3COOH$ | 260 cc |
| $H_2O$ | 400 cc |

This mixture was then heated up to 130° C and into the autoclave there was continually fed at a flow rate of 165 normal liters/hour (Nl/h) a gaseous mixture containing 24% by volume of $C_2H_4$, 67% b.v. of $C_2H_6$ and 9% b.v. of $O_2$, while the gaseous mixture was discharged at a rate that maintained the pressure at 25 atmospheres. After 5 hours the flow of gas was stopped.

The reaction mixture was brought down to room temperature and the reaction solution was then analyzed by the gas-chromatograph. The presence of 0.23 moles of glycol, 0.22 moles of monoacetate of the glycol and 0.04 moles of diacetate was measured. The mean productivity amounted to 8.5 grams/hour and per liter of solution, in terms of glycol. The percentage of glycol with respect to the sum total of the found products was 47%.

EXAMPLE 2

Into the same autoclave as described in Example 1 were introduced:

| | |
|---|---|
| $I_2$ | 0.040 moles |
| $Cu(OCOCH_3)_2 \cdot H_2O$ | 0.100 moles |
| $Ce(OCOCH_3)_3$ | 0.250 moles |
| $Mn(OCOCH_3)_2$ | 0.200 moles |
| $CH_3COOH$ | 260 cc |
| $H_2O$ | 400 cc |

The $CH_3COOH / H_2O$ ratio is about 40:60 by weight and 17:83 in moles. The procedure of Example 1 was repeated and there were obtained 0.370 moles of glycol, 0.280 moles of monoacetate and 0.030 moles of diacetate, with a percentage of glycol equal to 55%; the mean productivity in terms of glycol was 12.4 g/h/lt.

EXAMPLE 3

Example 2 was repeated but raising the temperature up to 150° C; after only 3 hours there were obtained 0.790 moles of glycol, 0.430 moles of monoacetate and 0.076 moles of diacetate, with a glycol percentage of 61%. The productivity in terms of glycol proved to be 39 g/h/lt.

EXAMPLE 4

Example 3 was repeated, but doubling the quantity of iodine and of copper acetate. After 3 hours there were obtained 0.79 moles of glycol, 0.48 moles of monoacetate and 0.06 moles of diacetate. The percentage of glycol proved to be 60% while the productivity amounted to 39.5 g/h/lt.

EXAMPLE 5

Example 4 was repeated but halving the quantity of cerium and magnesium salts. After 3 hours there were obtained 0.650 moles of glycol, 0.400 moles of monoacetate and 0.056 moles of diacetate. The percentage of glycol obtained corresponded to 59%, while the productivity amounted to 33 g/h/lt.

EXAMPLE 6

Example 4 was repeated, but replacing the cerium acetate with an equimolar quantity of manganese acetate. After 3 hours there were obtained 0.69 moles of glycol, 0.37 moles of monoacetate and 0.04 moles of diacetate. The percentage of glycol amounted to 63% while the productivity amounted to 32.5 g/h/lt.

EXAMPLE 7

In this test there were used only 20% of the copper and iodine used in the test of Example 4. After 3 hours there were obtained 0.360 moles of glycol, 0.300 moles of monoacetate and 0.027 moles of diacetate, with a glycol percentage of 52.5%. The productivity turned out to be equal to 20.5 g/h/lt.

EXAMPLE 8

Example 4 was repeated but raising the temperature up to 160° C. After 3 hours there were obtained: 0.83 moles of glycol, 0.38 moles of monoacetate and 0.04 moles of diacetate. In the discharge gases, differently from the preceding examples, we noted presence of a consistent quantity of $CO_2$.

EXAMPLE 9

Example 8 was repeated, but bringing the temperature up to 170° C. Thereby were obtained definitely less satisfying results.

EXAMPLE 10

Into the autoclave described in Example 1 were introduced:

| | |
|---|---|
| $I_2$ | 0.079 moles |
| $Cu(OCOCH_3)_2 \cdot H_2O$ | 0.190 moles |
| $Ce(OCOCH_3)_3$ | 0.110 moles |
| $Ce(NO_3)_3 \cdot 6H_2O$ | 0.100 moles |
| $CH_3COOH$ | 260 cc |
| $H_2O$ | 400 cc |

This mixture was heated up to 130° C and was then continuously fed with 163 Nl/h of a gas containing 18.4% b.v. of $C_2H_4$, 44.8% b.v. of $C_3H_8$ (propane), 36.8% of air. The gases were discharged at a rate that maintained the pressure at 25 atmospheres. After 5 hours the flow was stopped. Thereby were obtained: 0.300 moles of glycol, 0.320 moles of monoacetate and 0.090 moles of diacetate, with percentages of glycol of 42% and with a productivity of 12.4 g/h/lt.

EXAMPLE 11

Into the autoclave of Example 1 were introduced:

| | |
|---|---|
| $I_2$ | 0.079 moles |
| $Cu(OCOCH_3)_2 \cdot H_2O$ | 0.190 moles |
| $Ce(NO_3)_3 \cdot 6H_2O$ | 0.100 moles |
| $Mn(OCOCH_3)_2$ | 0.150 moles |
| $CH_3COOH$ | 260 cc |
| $H_2O$ | 400 cc |

The reaction mass was heated up to 130° C and into it was continuously fed at a flow rate of 165 Nl/h a gaseous mixture of the following volumetric composition: $C_2H_4$ 24.2%, $O_2$ 9.1%, $C_2H_6$ 66.7%. The gases were discharged at a rate that ensured the maintenance of a pressure of 25 atmospheres. After 5 hours the gas flow was stopped. There were obtained 0.540 moles of glycol, 0.520 moles of monoacetate and 0.045 moles of diacetate, with a glycol percentage of 49%. The productivity proved to be 19.5 g/h/lt.

EXAMPLE 12

Into the autoclave of Example 1 were introduced:

| | |
|---|---|
| $I_2$ | 0.079 moles |
| $Cu(OCOCH_3)_2 \cdot H_2O$ | 0.190 moles |
| $Ce(OCOCH_3)_3$ | 0.220 moles |
| $Ce(NO_3)_3 \cdot 6H_2O$ | 0.100 moles |
| $Mn(OCOCH_3)_2$ | 0.200 moles |
| $CH_3COOH$ | 260 cc |
| $H_2O$ | 400 cc |

The reaction mass was then heated up to 130° C and into it were continuously fed 165 Nl/h of a gas containing 23% of $C_2H_4$ (by volume), 66% b.v. of $C_2H_6$ and 11% b.v. of $O_2$. The gases were discharged at a rate that kept the pressure at 25 atm. After 3 hours the gas flow was stopped. There were obtained 0.55 moles of glycol, 0.38 moles of monoacetate and 0.047 moles of diacetate. The percentage of glycol corresponded to 55% while the productivity amounted to 30 g/h/lt.

EXAMPLE 13

Example 12 was repeated, but by raising the temperature up to 150° C. After only 1 hour of reaction there were obtained 0.55 moles of glycol, 0.40 moles of monoacetate and 0.05 moles of diacetate, with a percentage of glycol of 55%. The productivity amounted to 88.5 g/h/lt.

All the results of the preceding examples have been recorded on the following table.

TABLE

| Ex. | Activating ions | Temp. (° C) | Glycol percentage (%) | Productivity g/h/l in terms of glycol |
|---|---|---|---|---|
| 1 | Cu, Ce | 130 | 47 | 8.5 |
| 2 | Cu, Ce, Mn | 130 | 55 | 12.4 |
| 3 | Cu, Ce, Mn | 150 | 61 | 39 |
| 4 | Cu, Ce, Mn | 150 | 60 | 39.5 |
| 5 | Cu, Ce, Mn | 150 | 59 | 33 |
| 6 | Cu, Mn | 150 | 63 | 32.5 |
| 7 | Cu, Ce, Mn | 150 | 52.5 | 20.5 |
| 8 | Cu, Ce, Mn | 160 | 66.5* | 37* |
| 9 | Cu, Ce, Mn | 170 | —* | —* |
| 10 | Cu, Ce, Mn, $NO_3$ | 130 | 42 | 12.4 |
| 11 | Cu, Ce, Mn, $NO_3$ | 130 | 49 | 19.5 |
| 12 | Cu, Ce, Mn, $NO_3$ | 130 | 55 | 30 |
| 13 | Cu, Ce, Mn, $NO_3$ | 150 | 55 | 88.5 |

*presence of a considerable amount of $CO_2$; poor yield with respect to $C_2H_4$.

EXAMPLE 14

Into an enameled 2 liter autoclave were introduced:

| | |
|---|---|
| $I_2$ | 25 g (0.10 moles) |
| $Ce(OCOCH_3)_3$ | 63 g (0.20 moles) |
| $Cu(OCOCH_3)_2 \cdot H_2O$ | 50 g (0.25 moles) |
| $CH_3COOH$ | 160 cc |
| $H_2O$ | 500 cc |

The temperature was then brought up to 120° C and the pressure was brought up to 21 atmospheres with ethylene, in 15 minutes. The pressure then dropped down to 20.5 atm. and was restored to 23.5 atm. by means of oxygen. After 3 hours the pressure dropped again to 16 atm. At this point the absorption stopped and the mixture was cooled down to 75° C and the gases were discharged through a trap, cooled down to −80° C, into a collecting flask. In the trap no product could be found.

In the gases there was no oxygen and only traces of $CO_2$ were found.

The reaction mixture was then left in the autoclave and the cycle was repeated twice again; the first time the pressure dropped to 7 amt. in 2 hours, while the second one dropped to 6.5 atm. in 3 hours. After completion, there was practically no free iodine left in the solution.

In order to single out possible low-boiling products, 200 cc of the solution were distilled, having been connected to a trap kept at −50° C, but the research gave a negative result. An additional 200 cc were extracted with ether and the extract was analyzed by means of gas chromatography; the analysis showed the presence of the following products:

| | |
|---|---|
| ethylene-glycol | 4.1 g (0.066 moles) |
| ethylene-glycol monoacetate | 35.6 g (0.340 moles) |
| ethylene-glycol diacetate | 2.0 g (0.014 moles) |

EXAMPLE 15

Into the same autoclave of Example 14 were introduced:

| | |
|---|---|
| Cu I | 40 g (0.22 moles) |
| $CuCl_2 \cdot 2H_2O$ | 9 g (0.05 moles) |
| $CH_3COOK$ | 68 g (0.70 moles) |
| $H_2O$ | 500 cc |
| $CH_3COOH$ | 160 cc |
| propylene | 101 g |

The temperature was brought up to 120° C and there was recorded a pressure of 23.5 atm.; this pressure was then brought up to 29 atm. with oxygen, and during the test the pressure was maintained constant by restoring the oxygen consumed. After 5 hours the mixture was cooled down to room temperature. Two hundred cubic centimeters of the reaction mixture were extracted with ether and the extract was analyzed by gas-chromatography. The quantity of monoacetate propyleneglycol amounted to 27 g (0.23 moles).

EXAMPLE 16

Into the same autoclave as that described in Example 14 were introduced:

| | |
|---|---|
| $I_2$ | 25.4 g (0.10 moles) |
| $CH_3COOK$ | 68 g (0.70 moles) |
| $Cu(OCOCH_3)_2 \cdot H_2O$ | 50 g (0.25 moles) |
| $H_2O$ | 500 cc |
| $CH_3COOH$ | 160 cc |
| propylene | 100 g |

The temperature was then brought up to 120° C and there was recorded a pressure of 22 atm. Thereupon oxygen was introduced until there was obtained a total pressure of 28 atm. while the consumed oxygen was reintegrated. After 5 hours and 30 min. the mixture was cooled down to room temperature. Two hundred cubic centimeters of the reaction mixture were extracted with ether and the extract was then analyzed by gas-chromatography. The presence of the following products was ascertained:

| | |
|---|---|
| propylene-glycol | 3.6 g (0.048 moles) |
| propylene-monoacetate glycol | 21.1 g (0.180 moles) |
| propylene-diacetate glycol | 4.7 g (0.030 moles) |
| propylenic iodohydrine | 1.6 g (0.009 moles) |

EXAMPLE 17

Into the autoclave of Example 14 were introduced:

| | |
|---|---|
| KI | 33.4 g (0.2 moles) |
| $CH_3COOK$ | 19.6 g (0.2 moles) |
| $Cu(OCOCH_3)_2 \cdot H_2O$ | 60.0 g (0.3 moles) |
| $CH_3COOH$ | 200 cc |
| $H_2O$ | 500 cc |
| propylene | 103 cc |

The mixture was heated up to 120° C and the pressure rose to 3 atm. Thereupon oxygen was introduced until a total pressure of 29 atm. was obtained, and during the test the consumed oxygen was reintegrated. After 6 hours the mixture was cooled down to room temperature and 200 cc of the reaction mixture were extracted with ether and the extract was then analyzed by gas-chromatography. The following products were found to be present:

| | |
|---|---|
| propylene-glycol | 1.9 g (0.025 moles) |
| propylene-glycol-monoacetate | 19.8 g (0.170 moles) |
| propylene-glycol diacetate | 14.8 g (0.090 moles) |

Although the invention has herein above been illustrated by particular forms of embodiment, modifications may be introduced without thereby falling outside the scope of the invention itself.

What we claim is:

1. In a process for the manufacture of organic monoesters of vicinal glycols and the corresponding free glycols by reacting an olefin with oxygen, water and a carboxylic acid, in the liquid phase, and at a pH lower than 7, the improvement which comprises contacting the reaction mixture with a catalyst system consisting essentially of (i) iodine or an iodine compound selected from the group consisting essentially of copper iodide, manganese iodide, cerium iodide, an alkali metal iodide, an alkaline earth metal iodide and the iodohydrine of said olefin, (ii) a copper compound selected from the group consisting essentially of copper oxide, copper hydroxide, copper carbonate, copper iodide and a copper salt of said carboxylic acid, and (iii) an activating ion selected from the group consisting of manganese cation, cerium cation, an alkali metal cation, an alkaline earth metal cation, nitric anion, and mixtures of any of the foregoing, wherein the molar ratio of said carboxylic acid to water is lower than 1, the molar ratio of copper to water is equal to or lower than 2 moles of copper per 100 moles of water, and the molar ratio of iodine to copper is lower than 1.

2. A process according to claim 1 wherein the pH is lower than 5 and wherein the molar ratio of said organic acid to water is lower than 0.25 and the molar ratio of iodine to copper is between 0.05 and 0.50.

3. A process according to claim 1 wherein the temperature is in the range between 50° and 200° C.

4. A process according to claim 1 wherein the temperature is in the range between 130° and 160° C.

5. A process according to claim 1 wherein said process includes the step of feeding a gaseous into a reactor, said gaseous mixture consisting of oxygen, an excess of an olefin and an inert diluent.

6. A process according to claim 1 wherein said olefin is ethylene.

7. A process according to claim 1 wherein said olefin is propylene.

8. A process according to claim 1 wherein said carboxylic acid is acetic acid.

9. A process according to claim 5 wherein the inert diluent is ethane.

10. A process according to claim 1 wherein said manganese cation and said cerium cation are added in the form of a compound selected from the group comprising iodides, acetates and nitrates.

11. A process according to claim 1 wherein said nitric anion is added in the form of compound selected from the group comprising copper nitrate, cerium nitrate and manganese nitrate or mixtures thereof.

12. A process according to claim 1 wherein said nitric anion is formed in situ by the addition of nitrogen oxides.

* * * * *

UNITED STATES PATENT AND TRADEMARK OFFICE
CERTIFICATE OF CORRECTION

PATENT NO. : 4,061,868
DATED : December 6, 1977
INVENTOR(S) : Carlo Fumagalli et al It is certified that error appears in the above—identified patent and that said Letters Patent are hereby corrected as shown below:

In Col. 8, line 24, after "gaseous" and before "into, insert -- mixture --; on line 40, after "of" and before "compound", insert -- a --.

Signed and Sealed this

Eighteenth Day of April 1978

[SEAL]

Attest:

RUTH C. MASON
*Attesting Officer*

LUTRELLE F. PARKER
*Acting Commissioner of Patents and Trademarks*